United States Patent [19]

Balasubramanyan et al.

[11] 4,171,214
[45] Oct. 16, 1979

[54] PYRAZINE-2-YLMETHYL-KETONES AND THEIR FUNGICIDAL USE

[75] Inventors: Sugavanam Balasubramanyan, Wokingham; Margaret C. Shephard, Maidenhead, both of England

[73] Assignee: Imperial Chemical Industries Limited, London, England

[21] Appl. No.: 862,299

[22] Filed: Dec. 19, 1977

[30] Foreign Application Priority Data

Jan. 6, 1977 [GB] United Kingdom ............. 359/77

[51] Int. Cl.$^2$ .............. C07D 241/12; A61K 31/495; A01N 9/22
[52] U.S. Cl. ..................... 71/92; 544/336; 424/250
[58] Field of Search ............. 260/250 BN, 250 B; 544/336; 424/250; 71/92

[56] References Cited

U.S. PATENT DOCUMENTS

| | | | |
|---|---|---|---|
| 3,544,682 | 12/1970 | Taylor et al. | 544/336 |
| 3,794,642 | 2/1974 | Kress | 544/379 |
| 3,928,352 | 12/1975 | Taylor | 544/336 |
| 3,967,949 | 7/1976 | Benefiel et al. | 544/336 |

Primary Examiner—Jose Tovar

Attorney, Agent, or Firm—Cushman, Darby & Cushman

[57] ABSTRACT

A pyrazine compound of the formula:

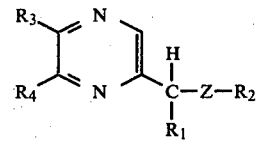

wherein $R_1$ and $R_2$ are hydrogen, or optionally-substituted hydrocarbyl, aryloxy or alkoxy and $R_2$, additionally may be pyridyl, thienyl or furyl; $R_3$ and $R_4$ are H, alkyl or aryl or together form a bridging group; Z is:

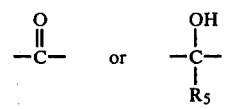

where $R_5$ is H, alkyl or aryl; and functional derivatives and salts thereof. The compounds are useful for combating fungal or bacterial diseases in plants.

7 Claims, No Drawings

PYRAZINE-2-YLMETHYL-KETONES AND THEIR FUNGICIDAL USE

This invention relates to pyrazine compounds useful as pesticides and also as plant growth regulating substances, to a process for preparing them, to compositions containing them and to a method of combating pests, especially fungi and bacteria, using them.

The invention provides pyrazine compounds having the general formula:

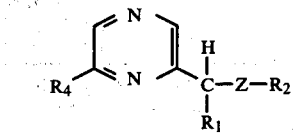

General Formula I wherein $R_1$ and $R_2$ are hydrogen, optionally-substituted hydrocarbyl, aryloxy or alkoxy and $R_2$, additionally, may be pyridyl, thienyl or furyl; $R_3$ and $R_4$ are H, alkyl or aryl or together form a bridging group; Z is:

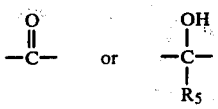

where $R_5$ is H, alkyl or aryl; and functional derivatives and salts thereof.

Functional derivatives are esters, ethers and metal complexes.

Suitable salts are salts with inorganic or organic acids, e.g. hydrochloric, nitric, sulphuric, toluenesulphonic, acetic or oxalic acid. The esters are suitably alkanoates (e.g. acetates) and the ethers are suitably alkyl (e.g. methyl or ethyl), aryl (e.g. phenyl) or aralkyl (e.g. benzyl) ethers.

The metal complex is suitably one including copper, zinc, manganese or iron.

The compounds of the invention contain chiral centres when $R_1$ is other than hydrogen. The compounds are generally obtained in the form of racemic mixtures. However these or other mixtures can be separated into the individual isomers by methods known in the art e.g. chromatography. In many cases, the compounds can be prepared stereospecifically in the form of a single diastereoisomer.

In a further aspect the invention provides pyrazine compounds having the general formula:

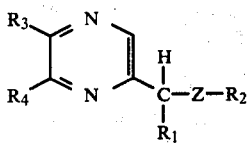

wherein $R_1$ and $R_2$ are hydrogen, or optionally-substituted hydrocarbyl, aryloxy or alkoxy; $R_3$ and $R_4$ are H, alkyl or aryl or together form a bridging group; Z is:

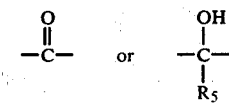

where $R_5$ is H, alkyl or aryl; and functional derivatives and salts thereof.

When $R_1$ and $R_2$ are hydrocarbyl groups they are preferably simple hydrocarbyl radicals in view of the ready availability of these. It is to be understood however that the whole range of hydrocarbyl groups, unsubstituted or substituted, is considered to fall within the scope of this invention since the particular nature of the hydrocarbyl group, if one is present, is not believed to be critically important. Thus the hydrocarbyl groups may be saturated or unsaturated, straight or branched chain, single-ring or multi-ring; thus $R_1$ may be, for example, alkyl, alkenyl, alkynyl, cycloalkyl, aryl, aralkyl, or alkaryl groups, for example methyl, ethyl, propyl, butyl, cyclohexyl, allyl or propynyl groups, and one or more of their hydrogen atoms may be substituted by simple substituents, such as, for example, halogen atoms, for example chlorine, bromine and fluorine, or pseudo halogen groups such as, for example cyano, or groups such as amino, hydroxy, nitro, phenyl and mercapto groups (which may themselves bear substituents).

When $R_1$, $R_2$, $R_3$ and $R_4$ are alkyl groups, or $R_1$ and $R_2$ are alkoxy groups, preferred alkyl and alkoxy groups are straight or branched chain groups having 1 to 4 carbon atoms and especially 3 or 4 carbon atoms; examples are methyl, ethyl, propyl (n-, iso- or t-butyl), methoxy or ethoxy. Preferred aryl groups or aryloxy groups, for $R_1$ are phenyl and phenoxy groups and halophenyl and halophenoxy groups. Particularly preferred aryl or aralkyl groups for $R_1$ are fluorobenzyl, chlorobenzyl, benzyl, fluorophenyl and chlorophenyl. Preferred groups for $R_2$ are branched and straight chain alkyl especially t-butyl, propyl and optionally-substituted phenyl especially halo-phenyl. Preferred substituents on any phenyl or phenoxy group for $R_1$ or $R_2$ are one or two halogens, and chlorine and fluorine especially. $R_3$ and $R_4$ are preferably hydrogen but when they together form a bridging group, a preferred such group contains 4 carbon atoms.

In a preferred aspect the invention provides pyrazine compounds having the general formula:

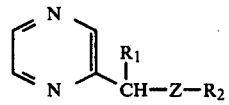

wherein Z is C=O or CHOH; $R_1$ is hydrogen, allyl, $C_1$ to $C_4$ alkyl especially butyl, phenyl, benzyl, phenoxy, mono- or di-, fluoro- or chloro-, -benzyl or -phenoxy; $R_2$ is $C_1$ to $C_4$ alkyl especially propyl or butyl, phenyl, or halophenyl; and functional derivatives and salts thereof.

In a particularly preferred aspect the invention provides pyrazine compounds having the general formula:

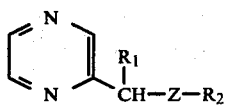

Z is C=O or CHOH, $R_1$ is fluoro-, chloro-, or dichloro-, -phenoxy or -benzyl; and $R_2$ is phenyl, halophenyl, propyl or butyl especially t-butyl.

Examples of the compounds of the invention are shown in Table I, and correspond to the general formula:

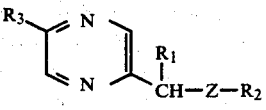

except for Compound No. 28, the full structure of which is set out in the Table.

TABLE 1

| COMPOUND NO | $R_1$ | $R_2$ | $R_3$ | Z | M.P. OR B.P. IN DEGREES CENTIGRADE |
|---|---|---|---|---|---|
| 1 | H | t-$C_4H_9$ | H | C=O | 74°–76°/0.08 mm |
| 2 | $CH_2$—⟨C$_6H_4$⟩—Cl | ⟨phenyl⟩ | H | C=O | 110°–112° |
| 3 | $CH_2$—⟨C$_6H_4$⟩—Cl | t-$C_4H_9$ | H | C=O | 96°–97° |
| 4 | n$C_4H_9$ | ⟨phenyl⟩ | H | C=O | 73°–74° |
| 5 | $CH_2$·CH=$CH_2$ | t-$C_4H_9$ | H | C=O | 100°–110°/0.1 mm |
| 6 | O—⟨C$_6H_4$⟩—Cl | t-$C_4H_9$ | H | C=O | 94°–96° |
| 7 | $CH_2$—⟨phenyl⟩ | ⟨phenyl⟩ | H | C=O | 131°–133° |
| 8 | $CH_2$—⟨C$_6H_4$⟩—$NO_2$ | t-$C_4H_9$ | H | C=O | 108°–110° |
| 9 | $CH_2$—⟨C$_6H_4$⟩—Cl | ⟨phenyl⟩ | H | CH·OH | 114°–117° |
| 10 | $CH_2$—⟨C$_6H_4$⟩—Cl | t-$C_4H_9$ | H | CH·OH | 97°–99° |
| 11 | $CH_2$—⟨C$_6H_3$(Cl)⟩—Cl | t-$C_4H_9$ | H | C=O | 102°–104° |
| 12 | H | ⟨phenyl⟩ | H | C=O | 83°–85 |
| 13 | H | ⟨thienyl⟩ | H | C=O | 51°–52° |
| 14 | n-$C_4H_9$ | ⟨C$_6H_4$⟩—Cl | H | C=O | 59°–62° |

TABLE 1-continued
| COMPOUND NO | R₁ | R₂ | R₃ | Z | M.P. OR B.P. IN DEGREES CENTIGRADE |
|---|---|---|---|---|---|
| 15 | 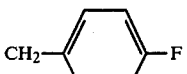 |  | H | C=O | 135°–136° |
| 16 | 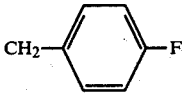 |  | H | C=O | 128°–130° |
| 17 | 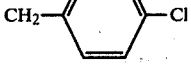 | n-C₃H₇ | H | C=O | 45°–46° |
| 18 | 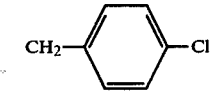 |  | H | C=O | 107°–109° |
| 19 | 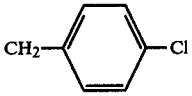 |  | H | C=O | 116°–118° |
| 20 | 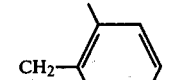 | t.C₄H₉ | H | C=O | 85°–87° |
| 21 | 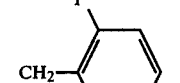 |  | H | C=O | 114°–116° |
| 22 | 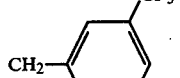 | t.C₄H₉ | H | C=O | oil |
| 23 | 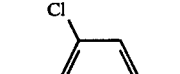 | n-C₃H₇ | H | C=O | 62°–64° |
| 24 | 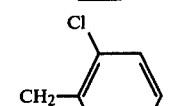 | t.C₄H₉ | H | C=O | 90°–100° |
| 25 | 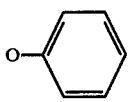 | t.C₄H₉ | H | C=O | 51°–53° |
| 26 | 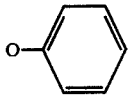 | t.C₄H₉ | H | C=O | 76°–78° |
| 27 | 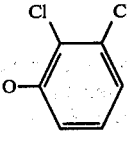 | t.C₄H₉ | H | C=O | 93°–95° |

TABLE 1-continued

| COMPOUND NO | R₁ | R₂ | R₃ | Z | M.P. OR B.P. IN DEGREES CENTIGRADE |
|---|---|---|---|---|---|
| 28 | 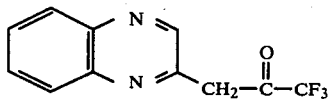 | | | | 144°–146° |

In this specification the numbering of the pyrazine ring is as follows:

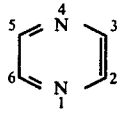

The majority of the pyrazine compounds of the invention may be made by the reaction of ketones of the general formula:

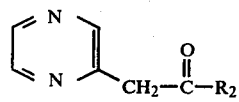

wherein $R_2$ is alkyl, aryl, or cycloalkyl with appropriately substituted alkyl, aralkyl, or alkenyl halides in the presence of base in hydroxylic or non-hydroxylic solvents. The resulting ketones are reduced using metal hydrides in a suitable solvent, or by using hydrogen in the presence of a suitable catalyst.

Alternatively the ketones mentioned in this invention could be made by alkylating 2-methylpyrazine with appropriately substituted organic halides and acylating them using suitable acylating agents. The synthetic sequence is depicted as shown below:

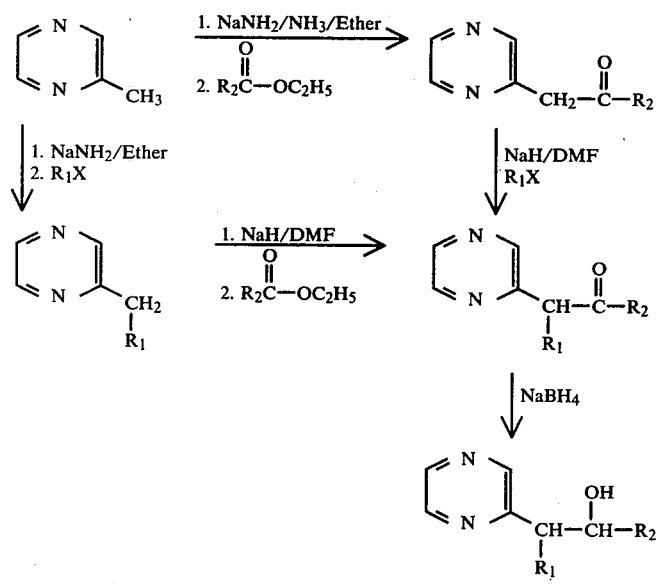

The α-aryloxypyrazines may be made by halogenating the aforementioned ketones of the formula:

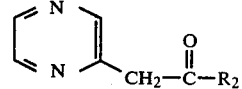

and displacing the halogen with an appropriately substituted phenol in the presence of a base in a suitable solvent.

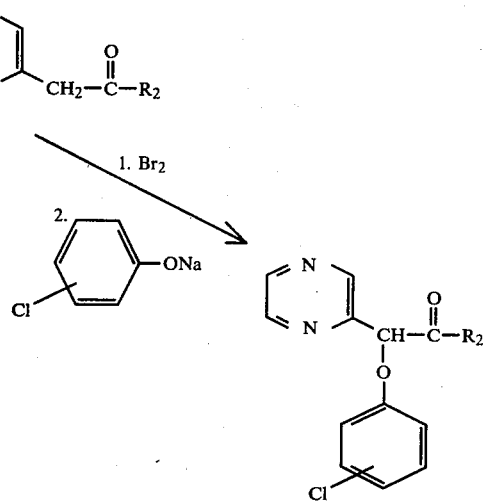

The salts, metal complexes, ethers and esters of the compounds of general formula (I) can be prepared from the latter in known manner. For example, the complexes can be made by reacting the uncomplexed compound with a metal salt in a suitable solvent.

The compounds are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Cercospora arachidicola* on peanuts and other Cercospora species on for example sugar beet, bananas and soya beans

*Botrytis cinerea* (grey mould) on tomatoes, strawberries, vines and other hosts

*Phytophthora infestans* (blight) on tomatoes and potatoes

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* or bananas). Further some of the compounds are active as seed dressings against: Fusarium spp., Septoria spp., Tilletia spp. (i.e. bunt, a seed borne disease of wheat), Ustilago spp., and Pyrenophora spp. on cereals.

They can also be used as industrial (as opposed to agricultural) fungicides, e.g. as paint film fungicides.

The compounds also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in cereals and soya bean where reduction in stem growth may reduce the risk of lodging. Compounds which induce stunting or dwarfing may also be useful in modifying the growth of sugar cane thereby increasing the concentration of sugar in the cane at harvest. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum,* and *perenne, Agrostis tenuis, Cynodon dactylon* (Bermuda grass), *Dactylis glomerata,* Festuca spp. (e.g. *Festuca rubra*) and Poa spp. (e.g. *Poa pratense*). At least some of the compounds will stunt grasses without significant phytotoxic effects and without deleteriously affecting the appearance (particularly the colour) of the grass; this makes such compounds attractive for use on ornamental lawns and on grass verges. The compounds can also stunt weed species present in the grasses; examples of such weed species are sedges (e.g. Cyperus spp.) and dicotyledonous weeds. The growth of non-crop vegetation (e.g. weeds or cover vegetation) can be retarded thus assisting in the maintenance of plantation and field crops. The plant growth regulating effect may manifest itself in an increase in crop yield.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. The treatment of plants with the compounds of the invention can lead to the leaves developing a darker green colour.

Further the compounds may inhibit the flowering of sugar beet and thereby may increase sugar yield. They may also reduce the size of sugar beet without reducing significantly the sugar yield thereby enabling an increase in planting density to be made.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds also have algicidal, anti-bacterial and anti-viral activities as well as herbicidal activity.

The compounds may be used as such for fungicidal or plant growth regulating purposes but are more conveniently formulated into compositions for such usage. The invention thus provides also a pesticidal, especially a fungicidal, or plant growth regulating, composition comprising a compound of general formula (I) or a salt, complex, ether or ester thereof as hereinbefore defined, and a carrier or diluent.

The invention also provides a method of combating fungal diseases in a plant, which method comprises applying to the plant, to seed of the plant or to the locus of the plant or seed a compound or salt, complex, ether or ester thereof as hereinbefore defined.

It also provides a method of regulating the growth of a plant, which method comprises applying to the plant, to seed of the plant or to the locus of the plant or seed a compound or salt, complex, ether or ester thereof as hereinbefore defined.

The invention compounds, salts, complexes, ethers and esters can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester complex thereof.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonionic agents. Suitable cationic agents are quaternary ammonium compounds, for example cetyl-trimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity [e.g. other growth stimulating substances such as the gibberellins (e.g. GA$_3$, GA$_4$ or GA$_7$), the auxins (e.g. indoleacetic or indolebutyric acid) and the cytokinins (e.g. kinetin, diphenylurea, benzimidazole and benzyladenine) and other compounds having complementary fungicidal or insecticidal activity], as well as stabilising agent(s), for example epoxides (e.g. epichlorhydrin). The other fungicidal compound can be one which is capable of combating ear diseases of cereals (e.g. wheat) such as Septoria, Gibberella, Helminthosporium and the sooty mould complex; examples of such compounds are benomyl, cardendazole (BCM) and captafol.

Alternatively, it can be one which is capable of combating other seed- and soil-borne or foliage diseases; examples of such compounds are Maneb and Captan.

The following Examples illustrate the invention; the temperatures are given in degrees Centigrade (°).

EXAMPLE 1

This Example illustrates the preparation of 1-phenyl-2-pyrazine-2′-yl-3-p-chlorophenylpropane-1-one (Compound 2, Table 1) of the formula:

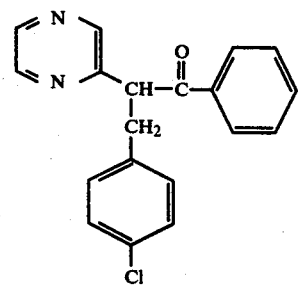

2-Phenacylpyrazine [J. Am. Chem. Soc., 81, 5159 (1959)] in dry dimethylformamide (20 ml) was added to a suspension of sodium hydride (35.0 mg) in dimethylformamide (5 ml). The mixture was stirred at room temperature for 4 hours and treated with p-chlorobenzyl chloride (2.44 g) dissolved in dimethylformamide (5 ml). After stirring for 3 hours at room temperature, the reaction mixture was poured into water, the resulting yellow solid was filtered off, washed with water, dried and recrystallised from ethyl acetate-petroleum ether (60°–80°). 1-Phenyl-2-pyrazine-2'-yl-3-p-chlorophenylpropane-1-one is obtained as a white crystalline solid.

EXAMPLE 2

This Example illustrates the preparation of 1-t-butyl-2-pyrazine-2'-yl-3-p-chlorophenylpropane-1-one (Compound 3, Table 1) of the formula:

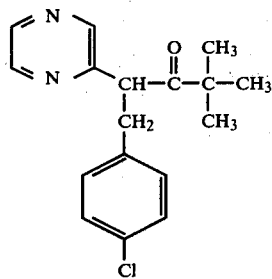

Pyrazine-2-yl-pinacolone [J. Am. Chem. Soc., 81, 5157-9 (1959)] in dry dimethylformamide (20 ml) was added to a suspension of sodium hydride. [400 mg (100%)] in dimethylformamide (5 ml). The reaction mixture was stirred at room temperature for 4 hours and treated with p-chlorobenzoyl chloride (2.74 g) dissolved in dimethyl formamide (5 ml). The reaction mixture was stirred for 3 hours at room temperature and poured into water. After work-up as described in Example 1, 1-t-butyl-2-pyrazine-2'-yl-3-p-chlorophenyl-propane-1-one was crystallised from petroleum ether (40°–60°).

Compounds 4, 5, 7, 8 and 11 of Table 1 were made in a similar manner as described in Examples 1 and 2 using the appropriate reactants.

EXAMPLE 3

This Example illustrates the preparation of α-pivaloyl-α-p-chlorophenoxy-2-methylpyrazine (Compound 6, Table 1) of the formula:

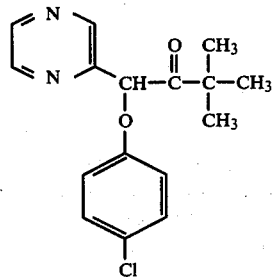

Stage I. Preparation of α-pivaloyl-α-bromo-2-methylpyrazine.

Bromine (0.9 ml) dissolved in acetic acid (5 ml) was added dropwise with stirring to pyrazine (3 g) in acetic acid (15 ml). The reaction was slightly exothermic and the mixture was stirred for 30 minutes and poured into water and extracted with ether. The ethereal layer was successively washed with water, sodium bicarbonate solution, water and dried (MgSO$_4$) and the solvent was removed to give α-pivaloyl-α-bromo-2-methylpyrazine as an orange oil which solidified on cooling. This was used in the next stage without further purification.

Stage II.

To a solution of sodium ethoxide [prepared by reacting sodium (270 mg) with ethanol (20 ml)] was added p-chlorophenol (1.5 g) with stirring. After 10 minutes, α-pivaloyl-α-bromo-2-methylpyrazine dissolved in ethyl acetate (10 ml) was added dropwise at room temperature and the reaction mixture was stirred for two hours. The mixture was filtered and the filtrate was concentrated in vacuo and diluted with water. The solution was extracted with ether and the ethereal layer was washed with water, dried (MgSO$_4$) and the solvent was removed in vacuo. The resulting yellow solid (the title compound) was recrystallized from petroleum ether (60°–80°).

EXAMPLE 4

This Example illustrates the preparation of 1-phenyl-3-p-chlorophenyl-2-pyrazine-2'-yl-propane-1-ol (Compound 9, Table 1), having the formula:

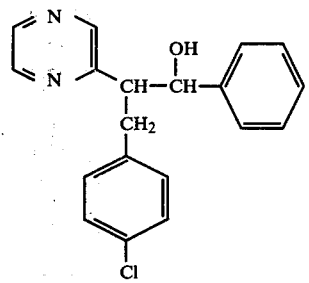

Sodium borohydride (350 mg) was added to a solution of 1-phenyl-3-p-chlorophenyl-2-pyrazine-2'-propane-1-one (3.0 g) in methanol (30 ml). After the slight exothermic reaction was finished, the reaction mixture was refluxed for one hour. The solvent was removed in vacuo, hydrochloric acid (40 ml of 1 N) was added when a white solid was obtained. This was filtered off, washed with water and dried. The title compound was crystallised from ethyl acetate/petroleum ether (60°–80°).

Compound No. 10 in Table 1 is also prepared in a similar manner using the appropriate ketone.

EXAMPLE 5

This Example lists a number of compositions of the invention.

(1) Dispersible Powder
Compound 11 (of Table I)—50% wt/wt
Aerosol OT—2%
Polyfon H—5%
China Clay—43%

(2) Emulsifiable Concentrate
Compound 11—100 g/liter
Amine dodecylbenzene sulphonate—400 g/liter
2-n-Butoxyethanol—to 1 liter (3) Aqueous Suspension
Compound 11—250 g/liter
Polyfon H—25 g/liter
Bentonite—15
Polysaccharide—0.75

Water—to 1 liter
(4) Dust
Compound 11—5% wt/wt
China clay—95%
(5) Granules
Compound 11—5% wt/wt
Starch—5%
China clay—90%
(6) Solvent solution
Compound 11—200 g/liter
Dimethylformamide—to 1 liter The other compounds of Table I were similarly formulated.

ment. After inoculation, the plants were put into an appropriate environment to allow infection to take place and then incubated until the disease was ready for assessment. The period between inoculation and assessment varied from 4 to 14 days according to the disease and invironment.

The disease control was recorded by the following grading:
4=No disease
3=0-5%
2=6-25%
1=26-60%
0=>60%

The results are shown in Table II.

TABLE 2

| COMPOUND NO | Puccinia recondita (wheat) | Phytophthora infestans (tomato) | Plasmopara viticola (vine) | Piricularia oryzae (rice) | Botrytis cinerea (tomato) | Erysiphe graminis (barley) |
|---|---|---|---|---|---|---|
| 1 | 0 | 0 | 0 | 2 | 0 | 4 |
| 2 | 1 | 0 | 0 | 0 | 0 | 4 |
| 3 | 1 | 0 | 0 | 0 | 0 | 4 |
| 4 | 0 | 0 | — | 0 | 0 | 4 |
| 5 | 1 | 0 | — | 1 | 1 | 4 |
| 6 | 0 | 0 | 0 | 0 | 0 | 4 |
| 7 | 1 | 1 | 0 | 0 | 0 | 3 |
| 8 | 1 | 2 | 0 | 3 | 4 | 4 |
| 9 | 1 | 2 | 0 | 0 | 4 | 3 |
| 10 | 0 | 0 | 2 | 0 | 2 | 4 |
| 11 | 0 | 0 | 0 | 0 | 1 | 4 |
| 12 | 0 | 0 | 0 | 2 | 0 | 3 |
| 13 | 1 | 0 | 0 | 0 | 2 | 0 |
| 14 | 1 | 0 | 0 | 0 | 2 | 4 |
| 15 | 0 | 0 | 0 | 1 | 1 | 4 |
| 16 | 1 | 1 | 0 | 1 | 0 | 4 |
| 17 | 0 | 1 | 2 | 2 | 0 | 4 |
| 18 | 1 | 0 | 0 | 1 | 3 | 4 |
| 19 | 0 | 0 | 0 | 0 | 2 | 4 |
| 20 | 2 | 0 | 0 | 0 | 2 | 4 |
| 21 | 1 | 0 | 0 | 1 | 3 | 3 |
| 22 | 0 | 0 | 0 | 0 | 0 | 4 |
| 23 | 2 | 0 | 1 | 0 | 0 | 4 |
| 24 | 0 | 0 | 0 | 1 | 2 | 4 |
| 25 | 1 | 3 | — | 2 | 0 | 4 |
| 26 | 0 | 2 | — | 3 | 1 | 4 |
| 27 | 1 | 2 | — | 0 | 1 | 4 |
| 28 | — | — | — | 1 | — | 1 |

EXAMPLE 6

The pyrazine compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment.

Compounds Nos 25 and 26 scored gradings of 3 and 4, respectively, against the disease *Cercospora arachidicola* (leaf spot) on peanuts.

We claim:

1. A pyrazine compound having the formula:

wherein Z is C=O; $R_1$ is hydrogen, allyl, $C_1$ to $C_4$ alkyl, phenyl, benzyl, phenoxy, nitrobenzyl, mono- or -di, fluoro- or chloro-, -benzyl or -phenoxy; $R_2$ is $C_1$ to $C_4$ alkyl, phenyl, or halophenyl; and and acid-addition salts thereof.

2. A pyrazine compound according to claim 1 wherein Z is C=O; $R_1$ is fluoro-, chloro-, or dichloro-, -phenoxy or -benzyl; and $R_2$ is phenyl, halophenyl, propyl or butyl.

3. A method for combating fungal or bacterial diseases in plants which comprises treating the plant, seed of the plant, or the locus surrounding the seed or plant with a pyrazine compound as claimed in claim 1.

4. A plant pesticidal or growth-regulating composition comprising, as an active ingredient, a pyrazine compound as claimed in claim 1; and a carrier or diluent.

5. A method of regulating the growth of a plant, which method comprises applying to the plant, to seed of the plant, or to the locus of the plant or seed, a compound as claimed in claim 1.

6. A pyrazine compound of the formula:

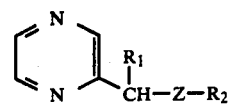

wherein Z is C=O, $R_1$ is benzyl, chlorobenzyl, fluorobenzyl, nitrobenzyl, or trifluoromethylbenzyl; and $R_2$ is $C_1$ to $C_4$ alkyl or phenyl.

7. A compound according to claim 6 wherein $R_1$ is chlorobenzyl and $R_2$ is butyl.

* * * * *